United States Patent [19]

Cousins

[11] 4,138,640

[45] Feb. 6, 1979

[54] MEASURING ARRANGEMENTS FOR ELECTRICAL CURRENTS

[75] Inventor: Charles P. Cousins, London, England

[73] Assignee: EMI Limited, Hayes, England

[21] Appl. No.: 682,159

[22] Filed: Apr. 30, 1976

[30] Foreign Application Priority Data

May 14, 1975 [GB] United Kingdom ............... 20282

[51] Int. Cl.² ............... A61B 6/02; G01R 19/00; G01R 23/00
[52] U.S. Cl. ............... 324/76 A; 250/445 T; 324/77 B
[58] Field of Search ............... 324/77 B, 76 A; 250/445 T

[56] References Cited

U.S. PATENT DOCUMENTS

| | | | |
|---|---|---|---|
| 2,137,133 | 11/1938 | Dallman | 324/76 A |
| 2,664,243 | 12/1953 | Hurvitz | 324/77 B |
| 3,745,317 | 7/1973 | Berthier et al. | 324/77 B |
| 3,903,401 | 9/1975 | Jayant | 324/77 B |

OTHER PUBLICATIONS

Woods et al., *Elementary Calculus,* 1928, pp. 64 and 65.

*Primary Examiner*—Alfred E. Smith
*Assistant Examiner*—T. N. Grigsby
*Attorney, Agent, or Firm*—Cooper, Dunham, Clark, Griffin & Moran

[57] ABSTRACT

An arrangement for measuring electrical currents is described, having advantageous application to the measurement of the small currents obtained from photodiodes associated with radiation sensitive detectors in a computerized axial tomographic apparatus. The arrangement involves a technique which, in effect, performs a least squares analysis on variation of the current from a detector over each of a succession of predetermined time intervals.

7 Claims, 1 Drawing Figure

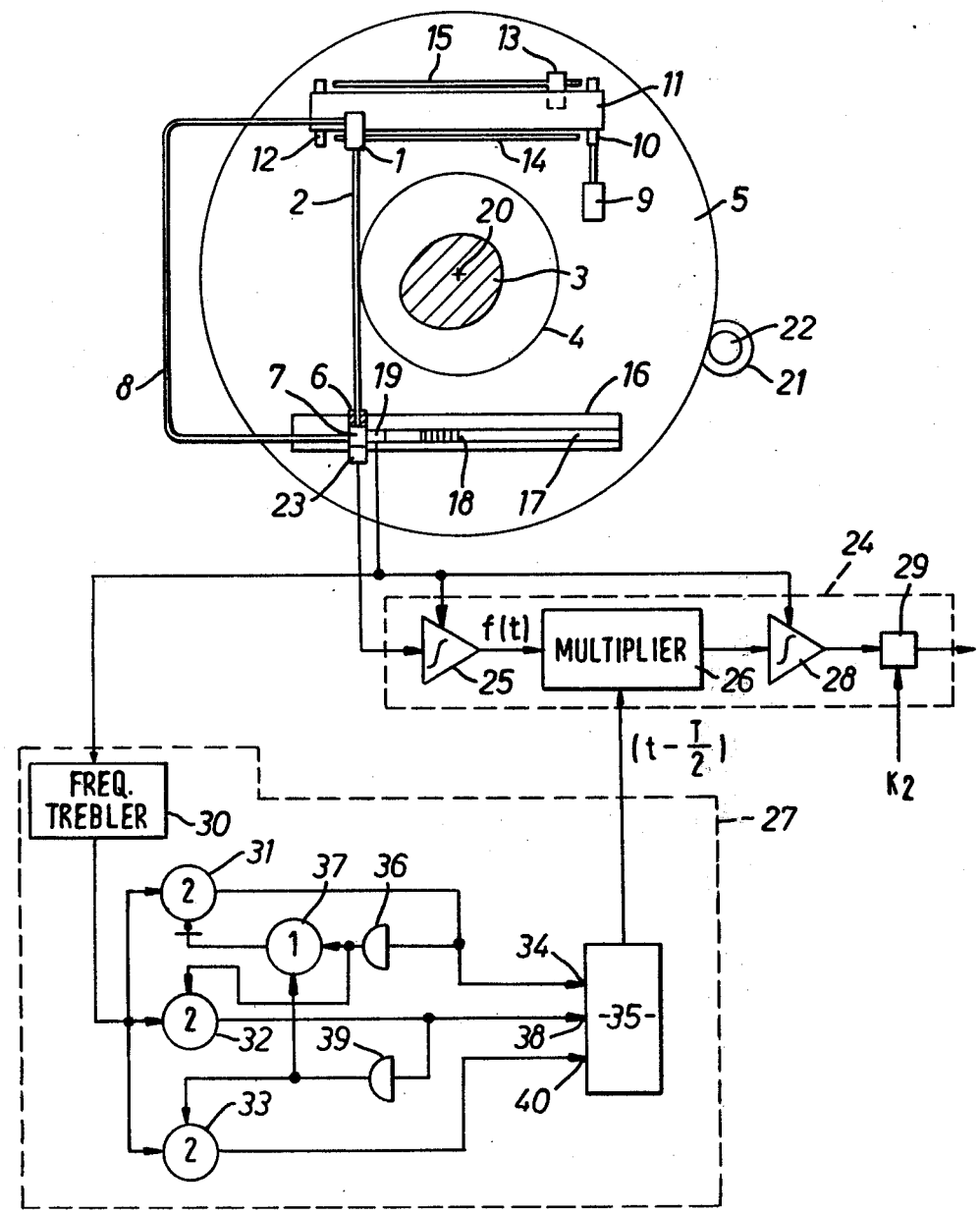

MEASURING ARRANGEMENTS FOR ELECTRICAL CURRENTS

The present invention relates to measuring arrangements for electrical currents, and it relates especially to such arrangements as may be used for accurately measuring small electrical currents in the presence of noise.

A technique which is used at present for measuring small direct currents is to integrate the current (together with the noise) over a fixed period and then to discharge the integrator at a known rate until its accumulated charge is zero. The discharge time is measured and used to calculate the mean level of the current prevailing over the integration period. The noise is assumed to be random, and thus to average to zero over the integration period. However, the amplitude of the noise signal which prevails at the end of the integration period can affect the time taken for the accumulated current to discharge to zero, and hence cause the calculation of the mean current to be in error. For example a noise 'spike' occurring at the very end of the integration period can increase the discharge time, causing the calculated value of the mean current to be too large.

It is an object of this invention to provide a measuring arrangement for electrical currents which reduces, at least to some extent, the problem discussed in the immediately preceding paragraph.

According to the invention there is provided a measuring arrangement for electrical current comprising means for sensing said current and for producing signals representative of said current during a prescribed time interval, a source of factor signals indicative of a function which exhibits a known variation during said time interval, means for combining said signals representative of said current with corresponding ones of said factor signals and means for integrating said combined signals for a period substantially equal to said prescribed time interval, to obtain a statistical estimation of the mean value of said current over said period.

In order that the invention may be clearly understood and readily carried into effect, an embodiment thereof will now be described, by way of example only, with reference to the accompanying drawing, the single FIGURE of which shows a general and elevational view of an apparatus which may advantageously incorporate an arrangement in accordance with the invention, and includes a block diagrammatic circuit for such an arrangement.

Referring now to the drawing, an advantageous application of the invention lies in its use to measure output current from a photodiode used to convert into electrical current the light output from a scintillator crystal used in a radiological apparatus of the kind described in U.S. Pat. No. 3,778,614. Such photodiodes produce rather small output currents, thus requiring a high gain amplifier to be used in the following circuits. Because of this, there is a tendency for circuit noise to become significant, and the invention exhibits the advantageous feature of reducing such noise by a considerable extent.

The radiological apparatus includes a source 1 of a pencil-like beam 2 of X-radiation which is directed through a body 3 disposed in an aperture 4 of a turntable member 5 and is incident via a collimator 6 upon a scintillator crystal 7 which gives an output in optical form, the brilliance of which is indicative of the amount of radiation incident thereon. The source 1 and the detector crystal 7 are linked by a rigid yoke 8 and can be scanned together laterally across the turntable member 5 by means of a reciprocating motor 9 mounted on the turntable member 5 and arranged to drive a toothed drive wheel 10 which, in turn, drives an endless, toothed belt 11 to which the source 1 is secured. Belt 11 passes over an undriven idler wheel 12 as well as the driven wheel 10, and a counter-balance weight 13 is secured to the opposite side of the belt 11 to the source 1 so that it moves in the opposite direction to source 1 at all times.

In addition, the source 1, counter-balance weight 13 and detector 7 move in respective linear guides 14, 15 and 16 on the turntable 5. The guide 16 for detector 7 also incorporates a graticule 17 of translucent material which bears evenly spaced opaque vertical lines such as those shown at 18. The lines are detected by means of a photocell and detector unit 19 which traverses with the detector 7 so as to provide timing pulses which are indicative of the progress of the aforementioned lateral scanning.

The turntable 5 can rotate about an axis 20 perpendicular thereto so as to cause all the components mounted thereon to rotate around the body 3. Turntable 5 is caused to rotate by means of a motor 21 which drives a gear wheel 22 that engages with teeth (not shown) formed around the periphery of turntable 5.

In operation, the motor 9 is first actuated to scan the source 1 and detector 7 laterally from left to right across the turntable 5, thus causing the pencil-like beam of X-radiation to irradiate, in turn, a set of parallel, co-planar paths through the body. Detector 7 produces outputs indicative of the amount of radiation emergent from the body along each path and these outputs are converted into electrical signals by means of a photodiode 23 which, of course, moves with the detector 7. When the source 1 and the detector 7 and photodiode 23 reach the right hand extremity of their traverse, the motor 21 is energised to rotate the turntable 5 through a small angle, such as $\frac{1}{2}°$. The motor 9 is then energised to drive the source 1 and detector 7 and photodiode 23 linearly from right to left across the turntable, so as to obtain output signals indicative of the amount of radiation passed through the body 3 along a second set of paths parallel to one another but inclined at $\frac{1}{2}°$ with respect to the first mentioned set. This procedure of alternate translational and rotational scans is continued until the total rotation executed by the turntable 5 is about 180° or more. All the output signals obtained during the investigation are processed, for example in the manner described in the aforementioned Patent Specification or in any other convenient way to evaluate the absorption coefficients, with respect to the radiation utilised, of each element in a two-dimensional array of elements notionally delineated in the plane of body 3 which has been irradiated.

The arrangement is accordance with the present example of the invention is shown as enclosed within the dashed outline 24. The output current from the photodiode 23 is applied to an integrator 25, which is reset periodically by means of timing pulses derived from the photocell/detector unit 19, these pulses being assumed to have a period T. The output of integrator 25, designated f(t), is applied to a multiplying circuit 26, where it is multiplied by a factor indicated as $(t - (T/2))$ for a purpose which will become clear hereinafter. In fact the actual signal $(t - (T/2))$, which would be a sawtooth passing through zero at $t = (T/2)$, is not used as such but is approximated by a square waveform generated by a circuit shown within the dashed outline 27, the square waveform being such as to have, during every period T, a value −1 for the time period t = 0 to t = (T/3), a value of 0 from t = (T/3) to t = (2T/3) and a value of +1 for the period t = (2T/3) to t = T. The output of multiplier 26 is applied to a second integrator circuit 28 which, like integrator 25, is re-set by means of the timing pulses of period T derived from unit 19. Circuit 28 provides output signals which are multiplied by a constant factor $K_2$ in a circuit 29, and the signals so multiplied constitute a measure of the mean value of the input current for the preceding period of time T, substantially free of the effects of noise, even that which occurs just prior to the end of the integration period.

The circuit within outline 27 comprises a frequency trebling circuit 30 which receives the pulse period T from unit 19 and produces therefrom pulses of period T/3, which pulses are applied to a set of three AND gates, 31, 32 and 33. The first AND gate 31 is arranged so that it is open all the time, except when a pulse is applied to its lower input terminal. The first pulse of each set of three from circuit 30 then passes straight through gate 31 and to a first input terminal 34 of a circuit 35 which is arranged on receipt of a pulse at terminal 34 to supply a multiplying factor of −1 continuously to the multiplying circuit 26. The pulse applied to terminal 34 is also applied to the input of a first delay component 36, which is arranged to impart a delay of T/3 to the pulse. The enable emergent from delay component 36 is applied as an enabling input to the second AND gate 32 and, via an OR gate 37, as a disabling input to the first AND gate 31. It will be appreciated that when this occurs, the second pulse of the set of three from circuit 30 is reaching the gates, and thus it is passed through gate 32 to a second input terminal 38 of circuit 35 causing the factor of −1 previously applied to circuit 26 to be discontinued and replaced by a factor of zero. In the same way as previously, the pulse passed by gate 32 to terminal 38 is also applied to the input of a second T/3 delay component 39; the output of delay component 39 being applied as an enabling input to gate 33 and, via the OR gate 37, as a disabling input to gate 31. Gates 31 and 32 are thus disabled, so that when the third pulse of a set arrives at the three gates, it passes through gate 33 and to a third input terminal 40 of circuit 35. This causes the zero factor applied previously to circuit 26 to be replaced by a factor of +1.

The first pulse of the next set of three, of course, passes through gate 31 to terminal 34 and thus the cycle of events recommences.

The invention is based upon the use of a form of analysis which is used in statistics to estimate the slope of the most accurate line drawn through a series of scattered points by utilising a form of least square error computation. If one considers a spatial distribution of points plotted in an x − y plane, the slope $\hat{b}$ of such a line is given by the expression:

$$\hat{b} = \frac{\sum_{j=1}^{n} x_j y_j - \frac{1}{n}\left(\sum_{j=1}^{n} x_j\right)\left(\sum_{j=1}^{n} y_j\right)}{\sum_{j=1}^{n} x_j^2 - \frac{1}{n}\left(\sum_{j=1}^{n} x_j\right)^2}$$

where n is the number of pairs of coordinates $(x_j, y_j)$ associated with the plotted points.

If this expression is transformed into the time domain, one obtains the new expression:

$$\hat{b} = T^3 \int_0^T (t - \frac{T}{2}) f(t) \, dt,$$

where T is the period of integration and f(t) is the output of the integrator 25. The x coordinate has been substituted by t time.

Also, the slope $\hat{b}$ is a function of time, t and current i so that $\hat{b} = k_1(i\,T)$, $k_1$ being a constant Thus for a given value of T, $$i = k_2 \int_0^T (t - \frac{T}{2}) \cdot f(t) \cdot dt,$$

where $k_2$ is a constant.

It will be observed that the circuit shown in the dashed outline 24 is one possible interpretation of the above expression for i.

The invention thus embodies a novel principle, that of effecting a statistical estimation of the mean value, over a period, of a current to be measured. This technique is particularly valuable when the current it is desired to measure is so small as to be immersed in noise. It is also valuable, however, in other circumstances, such as when the current itself is subjected to some variation, for example a normal or poisson distribution.

The current i can also be time varying, so long as the sampling frequency is at least twice as great as the maximum frequency of variation expected. The estimate is also independent of any offset in f(t).

It will be appreciated by those skilled in the art that the circuit shown within outline 24 is one example only of an arrangement in accordance with the invention, and that other embodiments can be constructed without departing from the scope of the invention.

Furthermore, although the invention has been described as applied to the radiological apparatus of FIG. 1, it is not limited to such an application. Moreover, if the invention is to be applied to such radiological apparatus, it will be appreciated that the apparatus need not assume the exact form shown in FIG. 1. In particular, the source 1 may be replaced by a source of a planar fan shaped swath of radiation in which case the detector 7 would be replaced by a bank of such detectors and a circuit such as shown within outline 24 would be provided for each detector. The angular steps of rotation effected by turntable 5 would, in such a case, be commensurate with the angle of the swath of radiation. Further the fan could be of such a wide angle as to span the whole body without the need for lateral scanning such as was executed in the apparatus of FIG. 1, the scanning being confined in such a case to a steady rotation of the turntable 5 relative to the body 3.

What I claim is:

1. A measuring arrangement for electrical current comprising an integrating circuit for receiving said current and for producing signals representative of the integral of said current during a prescribed time interval, means for producing factor signals indicative of a function which exhibits a known variation during said time interval, means for combining said signals representative of the integral of said current with corresponding ones of said factor signals to produce corresponding combined signals and a further integrating circuit for integrating said combined signals for a period substantially equal to said prescribed time interval, to obtain a statistical estimation of the mean value of said current over said period.

2. An arrangement according to claim 1 wherein said combining means comprises a multiplying circuit for multiplying said signals representative of the integral of said current with said corresponding ones of said factor signals.

3. An arrangement according to claim 1 wherein said means for producing the factor signals produce factor signals which comprises a linear ramp-like waveform.

4. An arrangement according to claim 1 including a further multiplying circuit for multiplying the integrated and combined signals by a substantially constant factor.

5. An arrangement according to claim 1 including means for generating timing pulses at a frequency corresponding to said time interval and for utilising said timing pulses to control the application of said factor signals to said combining circuits and the integration period of said integrating means.

6. An arrangement according to claim 1 wherein said means for producing said factor signals comprises means for producing a stepped waveform representing said factor signals.

7. An arrangement according to claim 6 wherein the means for producing said stepped waveform produce steps with amplitude and polarity which tend to deweight values of said current received by said first-mentioned integrating circuit toward the beginning of said prescribed time interval as compared with values of said current received by said mentioned integration circuit towards the end of said prescribed time interval.

* * * * *

UNITED STATES PATENT AND TRADEMARK OFFICE
CERTIFICATE OF CORRECTION

PATENT NO. : 4,138,640
DATED : February 6, 1979
INVENTOR(S) : CHARLES P. COUSINS It is certified that error appears in the above—identified patent and that said Letters Patent are hereby corrected as shown below:

Column 5, line 15 (Claim 3), "comprises" should read
-- comprise --.

Column 6, line 6 (Claim 5), "means" should read -- circuits --.

Signed and Sealed this

Eighth Day of July 1980

[SEAL]

Attest:

SIDNEY A. DIAMOND

Attesting Officer

Commissioner of Patents and Trademarks